United States Patent [19]

Umemura et al.

[11] 4,293,702
[45] Oct. 6, 1981

[54] METHOD FOR PREPARING 4-SUBSTITUTED-N-METHYLBENZO-THIAZOLONE DERIVATIVES

[75] Inventors: Takeaki Umemura; Haruki Morino, both of Takarazuka; Tetsuhiko Watanabe, Minoo; Tamon Uematsu, Toyonaka, all of Japan

[73] Assignee: Sumitomo Chemical Company, Limited, Osaka, Japan

[21] Appl. No.: 49,634

[22] Filed: Jun. 18, 1979

[30] Foreign Application Priority Data

Jun. 19, 1978 [JP] Japan .................................. 53-74614
Jun. 20, 1978 [JP] Japan .................................. 53-75111
Jun. 20, 1978 [JP] Japan .................................. 53-75112
Jul. 10, 1978 [JP] Japan .................................. 53-84161
Jul. 11, 1978 [JP] Japan .................................. 53-84859

[51] Int. Cl.³ .................. C07D 277/68; A61K 31/425
[52] U.S. Cl. ..................................... 548/165; 424/270
[58] Field of Search ......................................... 548/165

[56] References Cited

PUBLICATIONS

Hunter et al., "J. Chem. Soc.", pp. 1755–1761 (1935).

*Primary Examiner*—Donald G. Daus
*Assistant Examiner*—D. B. Springer
*Attorney, Agent, or Firm*—Wenderoth, Lind & Ponack

[57] ABSTRACT

A process for producing N-alkylbenzothiazolone derivatives of the formula (I),

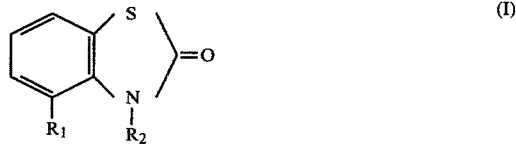

wherein $R_1$ is a hydrogen, chlorine, bromine, fluorine atom or a methyl group, and $R_2$ is an alkyl group having 1 to 5 carbon atoms, from 2-halogenobenzothiazole derivatives of the formula (II),

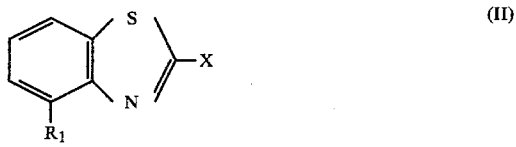

wherein $R_1$ is as defined above and X is a chlorine, bromine or fluorine atom, which is a starting material, through the intermediate of 2-alkoxybenzothiazole derivatives of the formula (III),

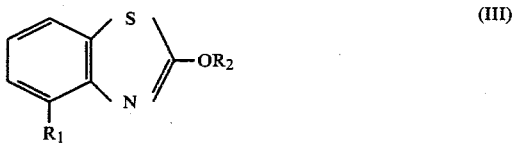

wherein $R_1$ and $R_2$ are as defined above, or benzothiazolone derivatives of the formula (IV),

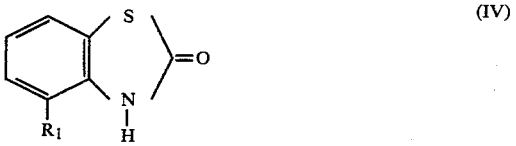

wherein $R_1$ is as defined above.

9 Claims, No Drawings

METHOD FOR PREPARING 4-SUBSTITUTED-N-METHYLBENZOTHIAZOLONE DERIVATIVES

The present invention relates to a process for producing N-alkylbenzothiazolone derivatives of the formula (I),

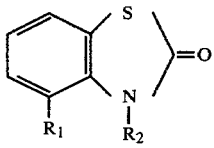

wherein $R_1$ is a hydrogen, chlorine, bromine, fluorine atom or a methyl group, and $R_2$ is an alkyl group having 1 to 5 carbon atoms, from 2-halogenobenzothiazole derivatives of the formula (II),

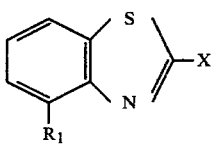

wherein $R_1$ is as defined above and X is a chlorine, bromine or fluorine atom, which is a starting material, through the intermediate of 2-alkoxybenzothiazole derivatives of the formula (III),

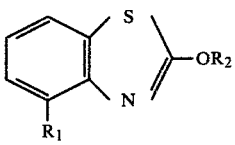

wherein $R_1$ and $R_2$ are as defined above, or benzothiazolone derivatives of the formula (IV),

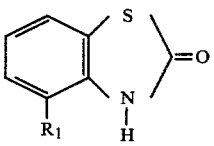

wherein $R_1$ is as defined above.

More particularly, it relates to a process for synthesizing N-alkylbenzothiazolone derivatives (I) in high purity and high yield (1) by reacting a 2-halogenobenzothiazole derivative (II) with a lower alkanol of the formula (V), $$R_2OH \quad (V)$$

wherein $R_2$ is as defined above, in the presence of a basic condensing agent to obtain a 2-alkoxybenzothiazole derivative (III), and carrying out the thermal rearrangement of the derivative (III) in the presence of a catalyst such as a tertiary amine, its salt, quaternary ammonium salt or dialkyl sulfate, or (2) by hydrolyzing a 2-halogenobenzothiazole derivative (II) to obtain a benzothiazolone derivative (IV), and reacting the derivative (IV) with an alkylating agent of the formula (VI), $$R_2Y \quad (VI)$$

wherein $R_2$ is as defined above and Y is a chlorine, bromine or iodine atom, or of the formula (VII), $$(R_2O)_2SO_2 \quad (VII)$$

wherein $R_2$ is as defined above, with an onium compound as catalyst in the presence of alkali metal hydroxide in an aqueous solution.

The N-alkylbenzothiazolone derivatives (I) according to the present invention are useful as non-medical fungicides as shown in Published Japanese Patent Application (unexamined) No. 90261/1978 and No. 124264/1978 and Japanese Patent Application No. 106192/1977. According to these prior art, these compounds are synthesized (1) by alkylation of a benzothiazolone derivative in a non-aqueous solvent in the presence of a strong base such as sodium hydride; (2) by N-alkylation of a 2-alkylthiobenzothiazole derivative followed by hydrolysis; (3) by thermal decomposition of a 2-nitrosoamino-3-alkylbenzothiazole derivative; or (4) by reaction of 2-mercaptoaniline derivative with phosgene.

But many difficulties are observed in carrying out these methods in industry because special operation conditions are required when expensive, dangerous sodium hydride is used, and because complicated by-products are produced so that purification such as recrystallization is necessary to obtain high-purity products, which leads to a low yield. Further, some other methods for carrying out the similar reaction of these homologues are known, but, as described hereinafter in detail, satisfactory results could not also be obtained when these known methods were applied to the compounds of the present invention.

As a result of extensive study on the synthesis of N-alkylbenzothiazolone derivatives (I), the inventors, contrary to the conventional informations, found a process for producing the objective compounds in high purity and high yield in an industrially advantageous manner. The inventors thus attained to the present invention.

The embodiments of the present invention will be illustrated below in detail for each reaction step, including informations on the prior arts.

PROCEDURE A: Preparation of 2-alkoxybenzothiazole derivatives (III) by the reaction of 2-halogenobenzothiazole (II) with alkanol (V) in the presence of a dehydrohalogenating agent A similar process for producing 2-alkoxybenzothiazole is described in the following literatures:
W. H. Davis et al., J. Chem. Soc., 304 (1942),
H. Gilman et al., J. Am. Chem. Soc., 74, 1081 (1952),
J. K. Elwood et al., J. Org. Chem., 32, 2956 (1967).

This process comprises reacting 2-halogenobenzothiazole with alkali metal alkoxide, previously prepared from an alcohol and alkali metal, in an absolute alcohol to produce 2-alkoxybenzothiazole.

But the industrialization of this known process was accompanied by many difficulties, when alkali metal alkoxide is prepared from an alkali metal and alcohol, caution must be taken because the reaction between an alkali metal and alcohol is so exothermic and an alkali metal has the property of reacting with water so as to cause ignition, combustion and explosion. Therefore, the alcohol should be completely water-free; and in order to recover and reuse the alcohol, dehydration and purification of the alcohol are essential. Consequently, this method has many drawbacks in terms of operation and safety, and besides the alkali metal is not so cheap.

Generally, reaction for synthesizing ethers from an alcohol and halogen compound is well known as the Williamson reaction (Shin Jikken Kagaku Kōza, Vol. 14 (1), 568 (1977), edited by Chemical Society of Japan, published by Maruzen Co.). Most commonly, ethers are synthesized by the reaction between an alkyl halide and alkoxide. Modified examples of the Williamson reaction, i.e. the reaction between an alkyl halide and alcohol in the presence of a base, are also known. In most of them, however, strong bases such as sodium amide, barium oxide, silver ozide, sodium hydride and the like are required, or, when weaker bases (e.g. potassium carbonate, triethylamine, sodium hydroxide) are used, limited special solvents, i.e. aprotic polar solvents (e.g. dimethyl sulfoxide, dimethylformamide, dimethoxyethane, tetrahydrofuran) are required in order to allow the reaction to proceed sufficiently. In fact, 2-halogenobenzothiazole can not be easily converted to its methoxy derivative in methanol in the presence of triethylamine, (refer to Comparative Example). These special bases or solvents are not suitable for industrial use in terms of safety and economy.

It is also known that 2-halogenobenzothiazole is easily hydrolyzed with an alkali to produce 2-hydroxybenzothiazole (benzothiazolone). Consequently, it has been considered that, when 2-halogenobenzothiazole is treated with an alkali metal hydroxide particularly in the presence of water, the formation of the 2-hydroxy compound as a by-product can not be avoided.

For example, it was reported that 2,6-dibromo-7-nitro-benzothiazole is converted to the 2-methoxy compound with sodium methoxide in a non-aqueous system in a low yield (34.2%) and the 2-hydroxy compound is produced in a fairly large amount as a by-product by hydrolysis on account of incomplete removal of moisture from the reaction system (R. C. Elderfield et al., J. Org. Chem., 18, 1092 (1953)).

As a result of extensive studies to overcome the foregoing drawbacks encountered in the production of 2-alkoxybenzothiazole derivatives (III), the inventors found that the objective derivatives (III) can be obtained easily, in a high yield and under very mild conditions by reacting a 2-halogenobenzothiazole derivative (II) with an alcohol in the presence of a basic condensing agent (e.g. alkali metal hydroxides, alkali metal carbonates, heterocyclic tertiary amines).

Further, it was found that the basic condensing agents used in the process of the present invention are also effective in the presence of water, the formation of the hydrolyzed by-product the 2-halogenobenzothiazole derivatives (II), i.e. 2-hydroxy compound (benzothiazolone) (IV), which is expected to be produced in large amounts from the conventional knowledge in the field, is generally limited to 1% or less, and that the objective 2-alkoxy compounds are obtained almost quantitatively.

It is very important as described in the following Procedure B that 2-alkoxybenzothiazole derivatives (III) can easily be changed to N-alkylbenzothiazolone derivatives (I), useful non-medical fungicides, by thermal rearrangement in the presence of a suitable catalyst.

As the essential basic condensing agent used as a dehydrohalogenating agent in the present invention, there may be given alkali metal hydroxides (e.g. sodium hydroxide, potassium hydroxide), alkali metal carbonates (e.g. sodium carbonate, potassium carbonate) and heterocyclic tertiary amines [1,5-diazabicyclo[3.4.0]nonene-5 (DBN), 1,5-diazabicyclo[5.4.0]undecene-5 (DBU), 1,4-diazabicyclo[2.2.2]octane (DABCO), 2-dimethylamino-1-pyrroline, 5-methyl-1-azabicyclo[3.3.0]octane].

The amount of the basic condensing agent per mole of 2-halogenobenzothiazole derivative is optional in a range above about 1.0 mole, but practically it is 1.0 to 2.2 moles.

As a solvent for the reaction, the alcohol, one of the reagents, and/or other various solvents, which do not disturb the present reaction in principle and are stable under the reaction conditions, may be used. The solvents include, for example, aliphatic hydrocarbons (e.g. hexane, heptane), aromatic hydrocarbons (e.g. benzene, toluene, xylene), halogenated aromatic hydrocarbons (e.g. chlorobenzene, dichlorobenzene) and ethers (e.g. diethyl ether, diisopropyl ether).

Water-miscible solvents among the foregoing solvents may be used as a mixture with water, and, dehydration and purification are not particularly necessary in recovering them. When a water-immiscible solvent is used and the base is not soluble in it, the present reaction may be carried out, with an aqueous solution of the base, in a two-phase system comprising an aqueous phase and an organic phase.

The reaction temperature may optionally be selected depending upon the reagents and solvents, but generally the reaction is carried out under mild conditions in the vicinity of room temperature (about 20° C.) to that of the refluxing temperature of the solvent.

PROCEDURE B: A process for producing N-alkylbenzothiazolone derivatives (I) characterized in that 2-alkoxybenzothiazole derivatives (III) obtained in Procedure A are subjected to thermal rearrangement in the presence of a catalyst such as a tertiary amine, its salt, quaternary ammonium salt or dialkyl sulfate A process for producing N-methylbenzothiazolone via 2-methoxybenzothiazole, by thermal rearrangement without solvent was disclosed in W. H. Davis et al., J. Chem. Soc., 304 (1942). Further, it was reported in the literature that iodine has no effect as a catalyst.

This process was comprised of prolonged heating at high temperature as an essential operation for accomplishing the rearrangement, and it has not a little difficulty in terms of yield, safety and energy consumption for carrying it out on an industrial scale.

It was also reported that 3-methyl-4-bromobenzothiazolone can be obtained by heating 2-methoxy-4-bromobenzothiazole at 160° C. for 5 hours, and that this reaction may also be carried out in an inert solvent such as nitrobenzene or dichlorobenzene (Uematsu et al., West German Patent Application No. 2801868). But the yield is only up to 86.7% and reference is not made to the use of catalyst in the patent.

As a result of extensive studies to overcome the foregoing drawbacks, the inventors found that the objective N-alkylbenzothiazolone derivatives (I) can be obtained easily, almost quantitatively under very mild conditions by allowing the rearrangement to proceed in the presence of a catalyst such as a tertiary amine, its salt, a quaternary ammonium salt or dialkyl sulfate.

The tertiary amine used in the present invention may be selected optionally. For example, it includes aliphatic tertiary amines (e.g. triethylamine, tri-n-propylamine, tri-n-butylamine, N,N,N',N'-tetramethylethylenediamine, N,N-diethylbenzylamine), aromatic tertiary amines (e.g. N,N-dimethylaniline, N,N-diethylaniline) and tertiary amines having a nitrogen-containing heterocyclic ring (e.g. pyridine, 1,5-diazabicyclo[3.4.0]nonene-5 (DBN), 1,5-diazabicyclo[5.4.0]undecene-5 (DBU)). From the standpoint of the reaction rate and the amount used, it is desired to use relatively strong bases such as aliphatic tertiary amines, DBN and DBU. These tertiary amines may be used as a reaction solvent at the same time.

Further, the tertiary amines may be used not only as a free amine but also in the form of their salts such as hydrochlorides, hydrobromides and sulfates.

The amount of the tertiary amine or its salt per mole of 2-alkoxybenzothiazole derivative (III) optionally ranges from a catalytic amount of about 1/1000 mole to large excess as a reaction solvent. It is desirable to use 5/1000 mole or more of relatively strong bases such as aliphatic tertiary amines, DBN and DBU, for reducing the reaction time to 1 hour or less.

As the quaternary ammonium salt used in the present invention, optional ones may be used. For example, there may be given tetra-n-butylammonium bromide, tetra-n-butylammonium chloride, tetra-n-butylammonium iodide, tetra-n-butylammonium hydroxide, triethylbenzylammonium chloride, triethylbenzylammonium bromide, triethylbenzylammonium iodide, trimethylbenzylammonium chloride, n-cetylpyridinium bromide, tetra-n-butylammonium hydrogen sulfate and tetra-n-butylammonium perchlorate.

The amount of the quaternary ammonium salt based on the 2-alkoxybenzothiazole derivative (III) is optional in a wide range. An increase in the amount is favourable for an increased reaction rate, at the same temperature. Practically, satisfactory effects are observed within a range of 1/1000 to 1/10 mole, particularly 1/1000 to 2/100 mole, per mole of said derivative (III). As reaction conditions, it is desirable to use 5/1000 mole or more of one member selected from tetra-n-butylammonium chloride, tetra-n-butylammonium bromide, tetra-n-butylammonium iodide, triethylbenzylammonium chloride, triethylbenzylammonium bromide, triethylbenzylammonium iodide and trimethylbenzylammonium chloride. In this case, the reaction time can be reduced to 1 hour or less.

A process using dialkyl sulfate for producing N-alkylbenzothiazolone derivatives was disclosed in W. A. Soxton, J. Chem. Soc., 470 (1939). The process comprises N-alkylation of 2-methylthiobenzothiazole with more than an equimolar amount of dimethyl sulfate followed by heating and hydrolyzing the resulting 2-methylthiobenzothiazole dimethylsulfate adduct with an aqueous sodium hydroxide solution. This process is fundamentally different from the process of the present invention in that 2-methylthio compound is used as a starting material and that hydrolysis of the methylthio group is carried out after N-methylation. In addition, it is necessary to use at least equimolar amount of dimethyl sulfate as an alkylating agent.

In the process of the present invention, the inventors unexpectedly found that the rearrangement of 2-alkoxybenzothiazole derivatives (III) is effected almost quantitatively and under very mild conditions in the presence of a catalytic amount of a dialkyl sulfate.

The dialkyl sulfate used in the present invention includes for example dimethyl sulfate and diethyl sulfate. Of these sulfates, dimethyl sulfate has a larger effect. The amount of dialkyl sulfate based on 2-alkoxybenzothiazole derivative (III) is optional in a wide range. An increase in the amount is favourable for reaction rate, provided that the temperature condition is same. Practically, however, 1/100 to 1/10 mole per mole of 2-alkoxybenzothiazole derivative is sufficient.

The thermal rearrangement of 2-alkoxybenzothiazole derivatives in the presence of a catalyst (e.g. tertiary amines, their salts, quaternary ammonium salts, or dialkyl sulfates) may be carried out either in the presence or absence of a solvent. As the organic solvent, aprotic organic solvents may be used, and preferably, there may be given solvents having a high solubilities of 2-alkoxybenzothiazole derivatives, for example aromatic hydrocarbons (e.g. toluene, o-, m- or p-xylene) as well as halogenated hydrocarbons (e.g. monochlorobenzene, dichlorobenzene).

The reaction temperature is optional above 100° C. or the melting point of N-alkylbenzothiazolone derivatives (I), when the solvent is not present. But generally, it is in a range of 100° to 150° C. While when the solvent is present, this reaction is carried out under relatively mild conditions in the vicinity of the refluxing temperature of the solvent.

PROCEDURE C: A process for producing N-alkylbenzothiazolone derivatives (I) comprising hydrolyzing a 2-halogenobenzothiazole derivative (II) to obtain a benzothiazolone derivative (IV), and reacting the derivative (IV) with a lower alkyl halide (VI) or dialkyl sulfate (VII) with an onium compound as catalyst in the presence of an aqueous alkali metal hydroxide solution.

The intermediate benzothiazolone derivatives (IV) can be obtained by the method disclosed in R. C. Elderfield et al., J. Org. Chem., 18, 1092 (1953). For example, 4-chlorobenzothiazolone is obtained, although in a low yield (46.2%), by reacting 2-bromo-4-chlorobenzothiazole with a 10% aqueous sodium hydroxide solution for 1.5 hours under reflux. The yield of this reaction could however be elevated to 89% by using a water/dioxane (1:1) mixed solvent according to the improved process by the inventors.

The following processes for the direct N-methylation of similar compounds are known:

(1) A process comprising the reaction of benzothiazolone compounds with methyl halide or dimethyl sulfate in a two-phase system of chloroform and a 25 to 30% aqueous potassium hydroxide solution. Hunter et al., J. Chem. Soc., 1755 (1935).

(2) A process comprising reacting benzoxazolone compounds with methyl halide or dimethyl sulfate in an alcoholic solution of potassium hydroxide. Close et al., J. Am. Chem. Soc., 71, 1265 (1949).

(3) A process comprising reacting benzoxazolone compounds with methyl halide or dimethyl sulfate in a solution of metal alkoxide in an alcohol. (ibid.)

In the process (1), however, conversion is poor because the reaction is carried out in a two-phase system comprising an organic phase and aqueous phase; and besides, since the hydrolysis of dialkyl sulfate proceeds competitively, dialkyl sulfate should be used in large amounts in order to increase the conversion of the required reaction.

The processes (2) and (3) were studied in detail by Close et al. (J. Am. Chem. Soc., 71, 1265 (1949)), and in the process (2), the yield is very poor irrespective of reaction in a homogeneous system when the solvent is methanol. Even when the solvent is high-boiling cellosolve (glycol monoethyl ether), the yield is of the order of only 62 to 76%, which may not be said to be satisfactory at all.

The inventors also traced the N-methylation process using methanol as solvent according to the method disclosed by Close et al. and re-confirmed that the conversion was poor and found as a novel fact that the longer reaction time for increasing the conversion results in unexpected and increased side reactions. After all, the inventors could not obtain the objective N-methylated compound in a high yield (Reference Example).

As to the process (3), it is described that the yield was markedly increased, for example, to 80 to 95% by replacing potassium hydroxide with alkali metal alkoxide.

Regarding the use of alkali metal alkoxide, essential to said method, this process has many drawbacks in terms of operation, safety and economy as described earlier. Consequently, the industrialization of this process was accompanied by many difficulties.

It was recently reported by Uematsu et al. that 3-methyl-4-chlorobenzothiazolone was obtained by reacting 4-chlorobenzothiazolone with sodium hydride in xylene under reflux for 1 hour, followed by the reaction with dimethyl sulfate, for 2 hours. But, the yield of 3-methyl-4-chlorobenzothiazolone was only up to 77.6%. Refer to published Japanese Patent Application (unexamined) No. 90261/78.

Uematsu et al. proposed that this N-alkylation may be carried out under the following three combinations of solvent and base.

(1) Solvent: benzene, toluene, xylene, etc.; base: potassium tertbutoxide, sodium methoxide, sodium hydride, etc.

(2) Solvent: methanol, ethanol, etc.; base: sodium methoxide, sodium ethoxide, sodium hydroxide, potassium hydroxide, etc.

(3) Solvent: water, aqueous organic solvent; base: sodium hydroxide, potassium hydroxide, etc.

The combination (1) has the following drawbacks: The base is relatively expensive; the solvent should be water-free; and the base should be handled under a nonaqueous state to avoid deterioration of the activity. Under the combinations (2) and (3), the conversion of N-alkylation is low and by-products are produced by cleavage of the thiazolone ring when the reaction time is prolonged (refer to Reference Example 1).

As a result of extensive studies to overcome these drawbacks, the inventors found that the objective N-alkylbenzothiazolone derivatives (I) can be obtained easily, in a high yield and under mild conditions by reacting a benzothiazolone derivative (IV) with an alkylating agent using an onium compound as a catalyst in an aqueous alkali metal hydroxide solution.

The onium compound includes for example quaternary ammonium compounds, quaternary phosphonium compounds and sulfonium compounds. As specific examples of the typical onium compound, there may be given tetra-n-butylammonium bromide, tetra-n-butylammonium chloride, tetra-n-butylammonium hydrogen sulfate, triethylbenzylammonium chloride, triethylbenzylammonium hydroxide, 3-phenoxybenzyltriethylammonium bromide, trimethylbenzylammonium chloride, tetramethylphosphonium iodide, tetra-n-butylphosphonium bromide, ethyl-2-methylpentadecyl-2-methylundecylsulfonium methylsulfate and the like.

The amount of the onium compound based on the benzothiazolone derivative (IV) is optional within a wide range. From the standpoints of yield and economy, however, it is practically about 1/5 to about 1/200 mole, preferably 1/20 to 1/100 mole, per mole of the derivative.

The amount of the alkali metal hydroxide (e.g. sodium hydroxide, potassium hydroxide) is optional above 1 mole per mole of the benzothiazolone derivative (IV). From the economical point of view, however, a range of 1.1 to 1.5 mole is sufficient.

The concentration of the aqueous alkali metal hydroxide solution is optional in a range of dilute concentration to saturated concentration. But relatively low concentrations, for example up to about 10 W/W%, provide more desirable results.

The amount of the alkylating agent (e.g. alkyl halide, dialkyl sulfate) is optional above 1 mole per mole of the benzothiazolone derivative (IV). But the amount of 1.0 to 1.5 mole is sufficient to complete this reaction.

This reaction may be carried out either in the presence or absence of an organic solvent. When the organic solvent is used, aprotic organic solvents substantially immiscible with water are preferred.

As such aprotic organic solvents, there may be given aliphatic or aromatic hydrocarbons (e.g. n-hexane, cyclohexane, benzene, toluene, o-, m- or p-xylene) as well as halogenated hydrocarbons (e.g. dichloromethane, dichloroethane, chloroform, carbon tetrachloride, monochlorobenzene).

The reaction temperature is optional above 0° C. But generally, the reaction is carried out under mild conditions in the vicinity of room temperature to that of the refluxing temperature of the solvent.

The present invention will be illustrated in more detail with reference to the following examples, but it is not of course intended to limit the invention to these examples alone.

All the purities were determined by gas chlomatography.

PROCEDURE A

EXAMPLE 1

2-Bromo-4-chlorobenzothiazole (6.21 g, 0.025 mole) and 94% sodium hydroxide (1.57 g, 0.037 mole) were added to methanol (100 c.c.), and the mixture was heated under reflux for 30 minutes. After cooling, water (100 c.c.) was added to the reaction solution, followed by ice-cooling. The deposited crystals were filtered and washed with water to obtain 4.68 g of 2-methoxy-4-chlorobenzothiazole. Yield 93.8%, purity 99.3%, m.p. 55°–57° C.

EXAMPLE 2

2,4-Dichlorobenzothiazole (10.21 g, 0.05 mole) and 94% sodium hydroxide (8.30 g, 0.075 mole) were added to a 50 (V/V) % water/methanol mixed solvent (150 c.c.), and the mixture was heated under reflux for 30 minutes. After cooling, water (100 c.c.) was added to the reaction solution, followed by ice-cooling. The deposited crystals were filtered and washed with water to obtain 9.22 g of 2-methoxy-4-chlorobenzothiazole. Yield 92.4%, purity 100%, m.p. 55°–57° C.

EXAMPLE 3

A mixture (5 g, 0.023 mole) of 2-bromo-4-chlorobenzothiazole and 2,4-dichlorobenzothiazole and 1,5- diazabicyclo[5.4.0]undecene-5 (DBU) (3.8 g, 0.025 mole) were added to methanol (80 c.c.), and the mixture was heated under reflux for 4 hours. After cooling, water (150 c.c.) was added to the reaction solution, followed by ice-cooling. The deposited crystals were filtered and washed twice with water to obtain 4.23 g of 2-methoxy-4-chlorobenzothiazole. Yield 92.5%, purity 98.5%, m.p. 55°–57° C.

EXAMPLE 4

A mixture (20.87 g, 0.1 mole) of 2-bromo-4-chlorobenzothiazole and 2,4-dichlorobenzothiazole and a 48.5% aqueous sodium hydroxide solution (17.28 g, 0.21 mole) were added to toluene (150 c.c.), and then methanol (16.12 g, 0.5 mole) was added dropwise thereto at room temperature. After the addition was finished, the reaction solution was heated to 50° C. and maintained at 50° C. for 4 hours. After cooling, the toluene layer was washed three times with water, and the solvent was removed under reduced pressure to obtain 19.92 g of 2-methoxy-4-chlorobenzothiazole as a pale yellow viscous liquid (solidified after cooling). Yield 99.8%, purity 96.0%, m.p. 54°–56° C.

EXAMPLE 5

A mixture of 2-bromo-4-methylbenzothiazole (11.41 g, 0.05 mole) and 94% sodium hydroxide (2.34 g, 0.055 mole) in methanol (100 c.c.) was heated under reflux for 4 hours. After methanol was removed by evaporation, the residue was dissolved in chloroform, and the chloroform solution was washed twice with water. The solvent was then removed under reduced pressure to obtain 8.86 g of 2-methoxy-4-methylbenzothiazole as a pale yellow viscous liquid (solidified after cooling). Yield 98.5%, purity 97.8%, m.p. 40°–42° C.

EXAMPLE 6

A mixture (20.87 g, 0.1 mole) of 2-bromo-4-chlorobenzothiazole and 2,4-dichlorobenzothiazole and 94% sodium hydroxide (4.68 g, 0.11 mole) in 95% ethanol (200 c.c.) was heated under reflux for 1 hour. After cooling, water (250 c.c.) was added to the reaction solution, followed by ice-cooling. The deposited crystals were filtered and washed with water to obtain 19.86 g of 2-ethoxy-4-chlorobenzothiazole. Yield 92.9%, purity 98.9%, m.p. 43°–45° C.

EXAMPLE 7

A mixture (11.30 g, 0.05 mole) of 2-bromo-4-chlorobenzothiazole and 2,4-dichlorobenzothiazole and 94% sodium hydroxide (2.34 g, 0.055 mole) in n-propanol (100 c.c.) was heated under reflux for 1 hour. Water was added and the alcohol was distilled azeotropically together with water. The resulting oily substance was extracted with chloroform, and the chloroform layer was washed with water. The solvent was removed under reduced pressure to obtain 11.12 g of 2-n-propoxy-4-chlorobenzothiazole as a yellow viscous liquid. Yield 97.7%, purity 98.9%, b.p. 106°–108° C./0.12 mmHg.

EXAMPLE 8

A mixture (11.30 g, 0.05 mole) of 2-bromo-4-chlorobenzothiazole and 2,4-dichlorobenzothiazole and 94% sodium hydroxide (2.34 g, 0.055 mole) in n-amyl alcohol (100 c.c.) was heated under reflux for 1 hour. Water was added and the alcohol was distilled azeotropically together with water. The resulting oily substance was extracted with chloroform, and the chloroform layer was washed with water. The solvent was then removed under reduced pressure to obtain 12.07 g of 2-n-amyloxy-4-chlorobenzothiazole as a yellow viscous liquid. Yield 94.3%, purity 97.5%, b.p. 124°–126.5° C./0.3 mmHg, m.p. 28° C.

EXAMPLE 9

A mixture (11.30 g, 0.05 mole) of 2-bromo-4-chlorobenzothiazole and 2,4-dichlorobenzothiazole and 94% sodium hydroxide (2.34 g, 0.055 mole) in isopropanol (100 c.c.) was heated under reflux for 1 hour. Water was added and the alcohol was distilled azeotropically together with water. The resulting oily substance was extracted with chloroform, and the chloroform layer was washed with water. The solvent was then removed under reducing pressure to obtain 10.92 g of 2-isopropoxy-4-chlorobenzothiazole as a yellow viscous liquid. Yield 95.9%, purity 97.7%, b.p. 95°–96° C./0.2 mmHg.

EXAMPLE 10

A mixture (11.30 g, 0.05 mole) of 2-bromo-4-chlorobenzothiazole and 2,4-dichlorobenzothiazole and 94% sodium hydroxide (2.34 g, 0.055 mole) in isobutanol (100 c.c.) was heated under reflux for 1 hour. Water was added and the alcohol was distilled azeotropically together with water. The resulting oily substance was extracted with chloroform, and the chloroform layer was washed with water. The solvent was then removed under reduced pressure to obtain 11.70 g of 2-isobutoxy-4-chlorobenzothiazole as a yellow viscous liquid. Yield 96.8%, purity 97.2%, b.p. 103.5°–105° C./0.15 mmHg.

EXAMPLE 11

2-Chlorobenzothiazole (8.48 g, 0.05 mole) and a 48% aqueous sodium hydroxide solution (4.78 g, 0.055 mole) were added to toluene (40 c.c.), and methanol (8.09 g, 0.25 mole) was added dropwise thereto at room temperature. After the addition was finished, the reaction mixture was heated to and kept at 70° C. for 4.5 hours. After cooling, the toluene layer was washed three times with water, and the solvent was removed under reduced pressure to obtain 8.17 g of 2-methoxybenzothiazole as a pale yellow viscoud liquid (solidified after cooling). Yield 98.9%, purity 96.8%, m.p. 31°–33° C.

COMPARATIVE EXAMPLE 1

A mixture of 2-bromo-4-chlorobenzothiazole (6.2 g, 0.025 mole) and triethylamine (2.8 g, 0.028 mole) in methanol (80 c.c.) was heated under reflux for 10 hours. The reaction solution was then sampled and the conversion to 2-methoxy-4-chlorobenzothiazole was determined by gas chromatography to be 20%.

PROCEDURE B

EXAMPLE 12

A mixture of 2-methoxy-4-methylbenzothiazole (2.69 g, 0.015 mole) and tetra-n-butylammonium bromide (97 mg, $3 \times 10^{-4}$ mole) was heated at 130° C. for 40 minutes with stirring. After cooling, the reaction mass was dissolved in chloroform, and the chloroform layer was washed with water. The solvent was then removed under reduced pressure to obtain 2.65 g of 4-methyl-N-methylbenzothiazolone as pale yellow crystals. Yield 98.5%, purity 99.0%, m.p. 122°–124° C.

EXAMPLE 13

Triethylbenzylammonium chloride (230 mg, 0.001 mole) was added to a solution of 2-methoxy-4-chlorobenzothiazole (4.00 g, 0.02 mole) in toluene (8 g) and the mixture was heated under reflux for 5 hours. After cooling, the toluene layer was washed with water, and the solvent was removed under reduced pressure to obtain 3.90 g of 4-chloro-N-methylbenzothiazolone as white crystals. Yield 97.5%, purity 99.1%, m.p. 130°–132° C.

EXAMPLE 14

A mixture of 2-methoxy-4-chlorobenzothiazole (5.00 g, 0.025 mole) and tetra-n-butylammonium bromide (162 mg, $5 \times 10^{-4}$ mole) was heated at 140° C. for 10 minutes with stirring. After cooling, the reaction mass was dissolved in chloroform, and the chloroform layer was washed with water. The solvent was then removed under reduced pressure to obtain 4.88 g of 4-chloro-N-methylbenzothiazolone as white crystals. Yield 97.6%, purity 98.8%, m.p. 130°–132° C.

EXAMPLES 15 TO 19

Reaction was carried out in the same manner as in Example 14 except that both of the catalyst and its amount or either of them were changed. The results are shown in Table 1.

TABLE 1

| | Catalyst | | | | 4-Chloro-N-methylbenzothiazolone | |
|---|---|---|---|---|---|---|
| Example | Quaternary ammonium salt | Amount added (mole/mole) | Reaction temperature (°C.) | Reaction time (min) | Yield (%) | Purity (%) |
| 14 | Tetra-n-butyl-ammonium bromide | 0.02 | 140 | 10 | 97.6 | 98.8 |
| 15 | | 0.005 | 140 | 15 | 99.0 | 99.8 |
| 16 | | 0.001 | 140 | 180 | 98.0 | 99.5 |
| 17 | Triethyl-benzyl-ammonium chloride | 0.01 | 140 | 20 | 100.0 | 99.9 |
| 18 | | 0.005 | 140 | 35 | 96.0 | 99.8 |
| 19 | | 0.001 | 140 | 215 | 99.3 | 99.5 |
| Comparative Example 1 (no catalyst) | | | 140 | 180 | — | 2.0 |
| Comparative Example 2 (no catalyst) | | | 180 | 480 | — | 60.0 |

EXAMPLE 20

A mixture of 2-methoxy-4-chlorobenzothiazole (3.00 g, 0.015 mole) and tri-n-butylamine (14 mg, $7.5 \times 10^{-5}$ mole) was heated at 140° C. for 1 hour with stirring. After cooling, the reaction mass was dissolved in chloroform, and the chloroform layer was washed with a 2% aqueous hydrochloric acid and then with water. The solvent was removed under reduced pressure to obtain 2.92 g of 4-chloro-N-methylbenzothiazolone as white crystals. Yield 97.3%, purity 99.9%, m.p. 132°–133° C.

EXAMPLE 21

A mixture of 2-methoxy-4-chlorobenzothiazole (3.00 g, 0.015 mole) and triethylamine (7 mg, $7 \times 10^{-5}$ mole) was heated at 140° C. for 30 minutes with stirring. After cooling, the reaction mass was dissolved in chloroform, and the chloroform layer was washed with 2% aqueous hydrochloric acid and then with water. The solvent was removed under reduced pressure to obtain 3.00 g of 4-chloro-N-methylbenzothiazolone as white crystals. Yield 100%, purity 99.3%, m.p. 130°–132° C.

EXAMPLE 22

A mixture of 2-methoxy-4-chlorobenzothiazole (3.00 g, 0.015 mole) and 1,5-diazabicyclo[5.4.0]undecene-5 (DBU) (12 mg, $7.5 \times 10^{-5}$ mole) was heated at 140° C. for 40 minutes with stirring. After cooling, the reaction mass was dissolved in chloroform, and the chloroform layer was washed with 2% aqueous hydrochloric acid and then with water. The solvent was then removed under reduced pressure to obtain 2.95 g of 4-chloro-N-methylbenzothiazolone as white crystals. Yield 98.3%, purity 98.5%, m.p. 129°–132° C.

EXAMPLE 23

A mixture of 4-chloro-2-methoxybenzothiazole (3.00 g, 0.015 mole) and dimethyl sulfate (95 mg, $7.5 \times 10^{-4}$ mole) was heated at 150° C. for 3 hours with stirring. After cooling, the reaction mass was dissolved in chloroform, and the chloroform layer was washed with an aqueous solution saturated with sodium carbonate and then with water. The solvent was removed under reduced pressure to obtain 2.99 g of 4-chloro-N-methylbenzothiazolone as white crystals. Yield 99.7%, purity 99.0%, m.p. 130°–132° C.

EXAMPLE 24

A mixture of 2-methoxy-4-chlorobenzothiazole (2.00 g, 0.01 mole) and tetra-n-butylammonium bromide (64 mg, $2 \times 10^{-4}$ mole) was heated at 100° C. for 90 minutes with stirring. After cooling, the reaction mass was dissolved in chloroform, and the chloroform layer was washed with water. The solvent was removed under reduced pressure to obtain 1.98 g of 4-chloro-N-methylbenzothiazolone as white crystals. Yield 99.0%, purity 99.7%, m.p. 130°–132° C.

EXAMPLE 25

A mixture of 2-methoxybenzothiazole (2.00 g, 0.012 mole) and tetra-n-butylammonium bromide 24 mg, $7 \times 10^{-5}$ mole) was heated at 120° C. for 2.5 hours with stirring. After cooling, the reaction mass was dissolved in chloroform, and the chloroform layer was washed with water. The solvent was removed under reduced pressure to obtain 1.85 g of N-methylbenzothiazolone as white crystals. Yield 92.5%, purity 96.0%, m.p. 73°–75° C.

EXAMPLE 26

A mixture of 2-ethoxy-4-chlorobenzothiazole (2.14 g, 0.01 mole) and tetra-n-butylammonium bromide (64 mg, $2 \times 10^{-4}$ mole) was heated at 150° C. for 3 hours with stirring. After cooling, the reaction mass was dissolved in chloroform, and the chloroform layer was washed with water. The solvent was then removed under reduced pressure to obtain 2.06 g of 4-chloro-N-ethylbenzothiazolone as pale yellow crystals. Yield 96.3%, purity 97.5%, m.p. 94°–98° C.

EXAMPLE 27

A mixture of 2-n-propoxy-4-chlorobenzothiazole (2.28 g, 0.01 mole) and tetra-n-butylammonium bromide (64 mg, $2 \times 10^{-4}$ mole) was heated at 150° C. for 7 hours with stirring. After cooling, the reaction mass was dissolved in chloroform, and the chloroform layer was washed with water. The solvent was removed under reduced pressure to obtain 2.16 g of 4-chloro-N-n- propylbenzothiazolone as a pale yellow viscous liquid (solidified after cooling). Yield 94.7%, purity 96.0%, m.p. 40°–45° C., b.p. 108°–109° C./0.2 mmHg.

EXAMPLE 28

A mixture of 2-n-amyl-4-chlorobenzothiazole (2.56 g, 0.01 mole) and tetra-n-butylammonium bromide (64 mg, $2 \times 10^{-4}$ mole) was heated at 150° C. for 10 hours with stirring. After cooling, the reaction mass was dissolved in chloroform, and the chloroform layer was washed with water. The solvent was then removed under reduced pressure to obtain 2.39 g of 4-chloro-N-n-amylbenzothiazolone as a yellow viscous liquid. Yield 93.4%, purity 93.6%, b.p. 124°–125° C./0.16 mmHg.

PROCEDURE C

EXAMPLE 29

4-Chlorobenzothiazolone (9.28 g, 0.05 mole) was dissolved in a solution of sodium hydroxide (3.19 g, 0.075 mole) in water (220 ml), and tetra-n-butylammonium bromide (0.48 g, 0.0015 mole) and toluene (80 ml) were added thereto. Methyl iodide (11.21 g, 0.075 mole) was added dropwise thereto at room temperature, and the mixture was stirred at room temperature for 30 minutes and then at 50° to 60° C. for 1 hour, followed by cooling and phase-separation. The toluene layer was washed once with water, and the solvent was removed under reduced pressure to obtain 9.58 g of 4-chloro-N-methylbenzothiazolone as pale yellow crystals. Yield 96.0%, purity 99.3%, m.p. 130°–132° C.

EXAMPLE 30

4-Chlorobenzothiazolone (9.28 g, 0.05 mole) was dissolved in a solution of sodium hydroxide (3.19 g, 0.075 mole) in water (220 ml), and tetra-n-butylammonium bromide (0.48 g, 0.0015 mole) and toluene (80 ml) were added thereto. Dimethyl sulfate (9.40 g, 0.075 mole) was added dropwise thereto at room temperature, and the mixture was stirred at room temperature for 1 hour, followed by phase-separation. The toluene layer was washed once with water, and the solvent was removed under reduced pressure to obtain 9.80 g of 4-chloro-N-methylbenzothiazolone as pale yellow crystals. Yield 98.2%, purity 98.2%, m.p. 130°–132° C.

EXAMPLE 31

4-chlorobenzothiazolone (9.28 g, 0.05 mole) was dissolved in a solution of sodium hydroxide (3.19 g, 0.075 mole) in water (220 ml), and benzyltriethylammonium chloride (0.34 g, 0.0015 mole) and toluene (80 ml) were added thereto. Dimethyl sulfate (9.40 g, 0.075 mole) was added dropwise thereto at room temperature, and the mixture was stirred at room temperature for 4 hours, followed by phase-separation. The toluene layer was washed once with water, and the solvent was removed under reduced pressure to obtain 8.97 g of 4-chloro-N-methylbenzothiazolone as pale yellow crystals. Yield 90.3%, purity 96.7%, m.p. 129°–131° C.

EXAMPLE 32

4-Chlorobenzothiazolone (9.28 g, 0.05 mole) was dissolved in a solution of sodium hydroxide (3.19 g, 0.075 mole) in water (500 ml), and tetra-n-butylammonium bromide (0.48 g, 0.0015 mole) and ethylene dichloride (300 ml) were added thereto. Dimethyl sulfate (9.40 g, 0.075 mole) was added dropwise thereto at room temperature, and the mixture was stirred at room temperature for 1 hour, followed by phase-separation. The ethylene dichloride layer was washed once with water, and the solvent was removed under reduced pressure to obtain 9.37 g of 4-chloro-N-methylbenzothiazolone as pale yellow crystals. Yield 93.9%, purity 98.7%, m.p. 130°–132° C.

EXAMPLE 33

4-Methylbenzothiazolone (4.13 g, 0.025 mole) was dissolved in a solution of sodium hydroxide (1.60 g, 0.0375 mole) in water (100 c.c.), and tetra-n-butylammonium bromide (0.24 g, $7.5 \times 10^{-4}$ mole) and toluene (40 c.c.) were added thereto. Dimethyl sulfate (4.70 g, 0.0375 mole) was added dropwise thereto at room temperature, and the mixture was stirred at room temperature for 1 hour, followed by phaseseparation. The toluene layer was washed once with water, and the solvent was removed under reduced pressure to obtain 4.31 g of 4-methyl-N-methylbenzothiazolone as white crystals. Yield 96.2%, purity 98.8%, m.p. 122°–124° C.

EXAMPLE 34

4-Fluorobenzothiazolone (4.23 g, 0.025 mole) was dissolved in a solution of sodium hydroxide (1.60 g, 0.0375 mole) in water (100 c.c.), and tetra-n-butylammonium bromide (0.24 g, $7.5 \times 10^{-4}$ mole) and toluene (40 c.c.) were added thereto. Dimethyl sulfate (4.70 g, 0.0375 mole) was added dropwise thereto at room temperature, and the mixture was stirred at room temperature for 1 hour, followed by phase-separation. The toluene layer was washed once with water, and the solvent was removed under reduced pressure to obtain 4.47 g of 4-fluoro-N-methylbenzothiazolone as white crystals. Yield 97.6%, purity 98.7%, m.p. 121.5°–123.5° C.

EXAMPLE 35

4-Bromobenzothiazolone (5.75 g, 0.025 mole) was dissolved in a solution of sodium hydroxide (1.60 g, 0.0375 mole) in water (100 c.c.), and tetra-n-butylammonium bromide (0.24 g, $7.5 \times 10^{-4}$ mole) and toluene (40 c.c.) were added thereto. Dimethyl sulfate (4.70 g, 0.0375 mole) was added fropwise thereto at room temperature, and the mixture was stirred at room temperature for 1 hour, followed by phase-separation. The toluene layer was washed once with water, and the solvent was removed under reduced pressure to obtain 6.00 g of 4-bromo-N-methylbenzothiazolone as white cyrstals. Yield 98.3%, purity 99.0%, m.p. 138°–140° C.

EXAMPLE 36

4-Chlorobenzothiazolone (4.64 g, 0.025 mole) was dissolved in a solution of sodium hydroxide (1.60 g, 0.0375 mole) in water (100 c.c.), and tetra-n-butylammonium bromide (0.24 g, $7.5 \times 10^{-4}$ mole) and toluene (40 c.c.) were added thereto. Diethyl sulfate (5.78 g, 0.0375 mole) was added dropwise thereto at room temperature, and the mixture was stirred at room temperature for 1 hour, followed by phase-separation. The toluene layer was washed once with water, and the solvent was removed under reduced pressure to obtain 5.24 g of 4-chloro-N-ethylbenzothiazolone as white crystals. Yield 98.1%, purity 98.5%, m.p. 96°–98.5° C.

EXAMPLE 37

Benzothiazolone (3.78 g, 0.025 mole) was dissolved in a solution of sodium hydroxide (1.60 g, 0.0375 mole) in water (100 c.c.), and tetra-n-butylammonium bromide (0.24 g, $7.5 \times 10^{-4}$ mole) and toluene (40 c.c.) were added thereto. Dimethyl sulfate (4.70 g, 0.0375 mole) was added dropwise thereto at room temperature, and the mixture was stirred at room temperature for 1 hour, followed by phase-separation. The toluene layer was washed once with water, and the solvent was removed under reduced pressure to obtain 4.14 g of N-methyl-benzothiazolone as white crystals. Yield 100%, purity 97.7%, m.p. 70°–73.5° C.

REFERENCE EXAMPLE

Potassium hydroxide (4.95 g, 0.075 mole) and 4-chlorobenzothiazolone (9.28 g, 0.05 mole) were dissolved in methanol (100 ml), and methyl iodide (11.21 g, 0.075 mole) was added dropwise thereto at room temperature. After stirring under reflux for 3 hours, aliquots were sampled and the conversion was determined by gas chromatography. It was found that 50% of 4-chlorobenzothiazolone, a starting material, remained unreacted. Thereafter, additional 8.78 g (0.133 mole) of potassium hydroxide and 25.71 g (0.172 mole) of methyl iodide were added in three portions, respectively during 7 hours under reflux, until the starting material completely disappeared. After cooling, water (200 ml) was added to the reaction solution. The separated crystals were filtered, washed with water and dried to obtain 7.49 g of yellowish orange crystals (m.p. 65°–67° C.). It was found by NMR and elementary analyses shown below that this product was not the objective 4-chloro-N-methylbenzothiazolone but methyl N-methyl-N-(2-chloro-6-methylthiophenyl)carbamate, a product resulting from cleavage of the thiazole ring.

| | Elementary analysis: | | | | |
|---|---|---|---|---|---|
| | C (%) | H (%) | N (%) | S (%) | Cl (%) |
| Calculated | 48.9 | 4.9 | 5.7 | 13.0 | 14.4 |
| Found | 49.3 | 4.6 | 6.1 | 12.7 | 14.1 |

What is claimed is:

1. A process for producing N-alkylbenzothiazolone derivatives having the formula:

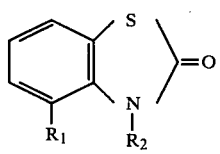

(I)

wherein $R_1$ is a hydrogen atom, chlorine atom, bromine atom, fluorine atom or methyl group, and $R_2$ is a $C_1$–$C_5$ alkyl group by heating a 2-alkoxybenzothiazole derivative at temperatures of 100°–150° C. without a solvent or by heating said derivative in a solvent at about the refluxing temperature of the solvent, said derivative having the formula:

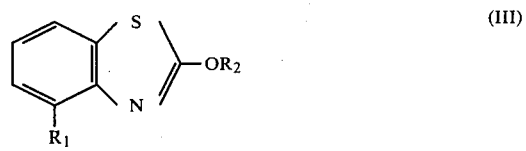

(III)

wherein $R_1$ and $R_2$ are defined above, in the presence of a catalytic amount of a catalyst selected from (1) teritary amines and salts thereof, which amines are selected from the group consisting of saturated hydrocarbyl aliphatic amines and diamines, dimethylaniline, N, N-diethylaniline, pyridine, 1,5-diazabicyclo[3.4.0], and 1,5-diazabicyclo[5.4.0]undecene-5 and the HCl and HBr and $H_2SO_4$ salts thereof; (2) a quaternary ammonium compound selected from the groups consisting of tetra-n-butylammonium bromide, tetra-n-butylammonium chloride, tetra-n-butylammonium iodide, tetra-n-butylammonium hydroxide, triethylbenzylammonium chloride, triethylbenzylammonium bromide, triethylbenzylammonium iodide, trimethylbenzylammonium chloride, n-cetylpyridinium bromide, tetra-n-butylammonium hydrogen sulfate and tetra-n-butylammonium perchlorate; and (3) a dialkyl sulfate selected from the group consisting of dimethyl sulfate and diethyl sulfate.

2. The process according to claim 1, wherein a tertiary amine is used as the catalyst in an amount of 1/1000 mole or more based on the 2-alkoxybenzothiazole derivative (III).

3. The process according to claim 2, wherein the tertiary amine is an aliphatic saturated amine, a 1,5-diazabicyclo[3.4.0]nonene-5 or 1,5-diazabicyclo[5.4.0]undecene-5 used as the catalyst in an amount of 5/1000 mole or more based on the 2-alkoxybenzothiazole derivative (III).

4. The process according to claim 1, wherein a quaternary ammonium salt is used as the catalyst in an amount of 1/1000 to 1/10 mole based on the 2-alkoxybenzothiazole derivative (III).

5. The process according to claim 4, wherein quaternary ammonium salt is selected from the group consisting of tetra-n-butylammonium chloride, tetra-n-butylammonium bromide, tetra-n-butylammonium iodide, triethylbenzylammonium chloride, triethylbenzylammonium bromide, triethylbenzylammonium iodide or trimethylbenzylammonium chloride and is used in an amount of 5/1000 mole or more based on the 2-alkoxybenzothiazole derivative (III).

6. The process according to claim 1, wherein an dialkyl sulfate is used as the catalyst in an amount of 1/100 to 1/10 mole based on the 2-alkoxybenzothiazole derivative (III).

7. The process according to claim 1, wherein $R_1$ is a chlorine atom and $R_2$ is a methyl group.

8. A process according to claim 1, wherein the N-alkylbenzothiazolone derivative of the formula (I), is one produced by heating a 2-alkoxybenzothiazole derivative of the formula (III),

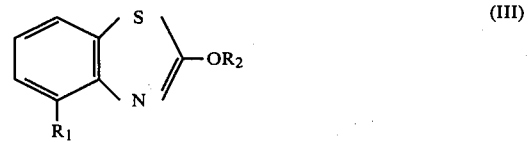

(III)

wherein $R_1$ and $R_2$ are defined as in claim 1.

9. The process according to claim 1, wherein $R_1$ is a chlorine atom and $R_2$ is a methyl group.

* * * * *